United States Patent
Pak et al.

(10) Patent No.: US 8,204,587 B2
(45) Date of Patent: Jun. 19, 2012

(54) APPARATUS FOR IONTOPHORESIS

(75) Inventors: Dong Sun Pak, Yongin-si (KR); Woo Chel Lee, Seongnam-si (KR)

(73) Assignee: Aram HUVIS Co., Ltd., Seongnam-si (KR)

( * ) Notice: Subject to any disclaimer, the term of this patent is extended or adjusted under 35 U.S.C. 154(b) by 395 days.

(21) Appl. No.: 12/515,269

(22) PCT Filed: Sep. 7, 2007

(86) PCT No.: PCT/KR2007/004338
§ 371 (c)(1),
(2), (4) Date: May 15, 2009

(87) PCT Pub. No.: WO2008/062943
PCT Pub. Date: May 29, 2008

(65) Prior Publication Data
US 2010/0241057 A1    Sep. 23, 2010

(30) Foreign Application Priority Data
Nov. 20, 2006    (KR) ................ 10-2006-0114405

(51) Int. Cl.
*A61N 1/30*    (2006.01)
*A61N 1/00*    (2006.01)
(52) U.S. Cl. .......................... 604/20; 607/63
(58) Field of Classification Search ............ 604/19–20; 607/1–3, 59, 62–63
See application file for complete search history.

(56) References Cited

U.S. PATENT DOCUMENTS

| | | | | |
|---|---|---|---|---|
| 4,764,164 A | * | 8/1988 | Sasaki | 604/20 |
| 5,042,975 A | * | 8/1991 | Chien et al. | 604/20 |
| 5,047,007 A | * | 9/1991 | McNichols et al. | 604/20 |
| 5,254,081 A | * | 10/1993 | Maurer et al. | 604/20 |
| 5,450,845 A | * | 9/1995 | Axelgaard | 600/382 |
| 5,688,232 A | * | 11/1997 | Flower | 604/20 |
| 5,785,040 A | * | 7/1998 | Axelgaard | 600/391 |
| 6,119,038 A | * | 9/2000 | Cook | 607/3 |
| 6,141,582 A | * | 10/2000 | Mori et al. | 604/20 |
| 6,148,232 A | * | 11/2000 | Avrahami | 604/20 |
| 6,760,618 B1 | * | 7/2004 | Inoue | 604/20 |
| 7,630,759 B2 | * | 12/2009 | Davies | 600/547 |
| 2001/0053885 A1 | * | 12/2001 | Gielen et al. | 604/20 |
| 2005/0039789 A1 | * | 2/2005 | Kim | 136/246 |
| 2007/0219480 A1 | * | 9/2007 | Kamen et al. | 604/20 |
| 2009/0048556 A1 | * | 2/2009 | Durand | 604/20 |
| 2009/0149800 A1 | * | 6/2009 | Durand | 604/20 |

(Continued)

FOREIGN PATENT DOCUMENTS

CA    2230815 A1    2/2011

(Continued)

*Primary Examiner* — Loan Thanh
*Assistant Examiner* — William Carpenter
(74) *Attorney, Agent, or Firm* — Christensen O'Connor Johnson Kindness PLLC

(57) ABSTRACT

The present invention relates to an iontophoresis apparatus, and more particularly, to an iontophoresis apparatus detachable from a mask or patch, wherein after skin condition is previously diagnosed before an iontophoresis is performed, the amount of current is adjusted according to the skin condition to absorb effective components contained in functional cosmetics or medicines into the skin, and a plurality of electrode pairs are applied to use interference current generated between the electrode pairs thereby accelerating absorption of the effective components and improving the skin condition.

9 Claims, 3 Drawing Sheets

U.S. PATENT DOCUMENTS

2009/0187134 A1 * 7/2009 Akiyama et al. ................ 604/20

FOREIGN PATENT DOCUMENTS

| | | |
|---|---|---|
| JP | 2001-95928 A | 4/2001 |
| KR | 1999-0044215 A | 6/1999 |
| KR | 2001-0002513 A | 1/2001 |
| KR | 100522927 B1 | 9/2005 |
| KR | 10-0513358 B1 | 2/2006 |
| KR | 100610253 B1 | 4/2006 |

* cited by examiner

[Fig. 1]
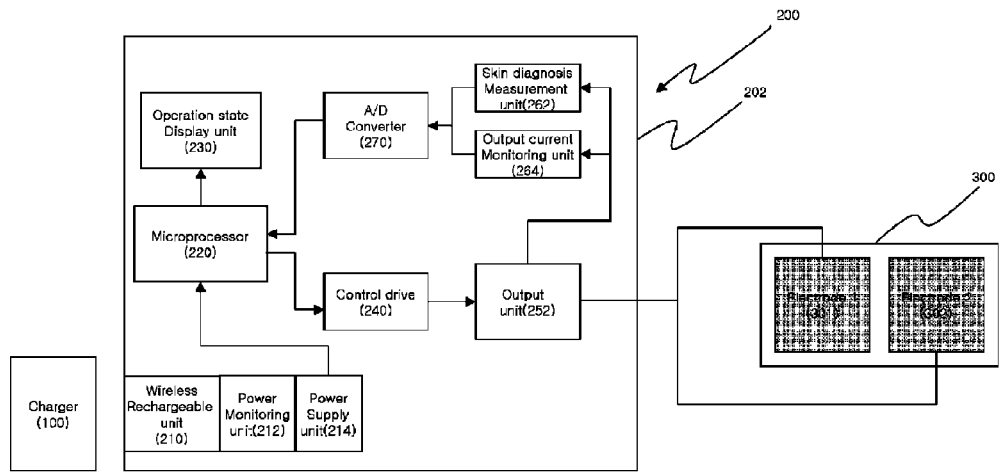
[Fig. 2]
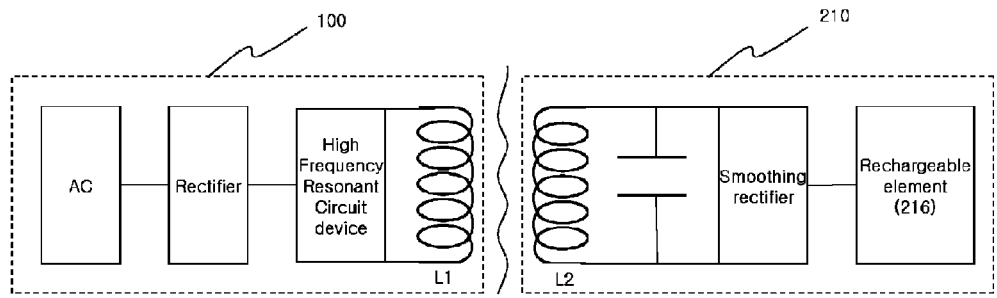
[Fig. 3]
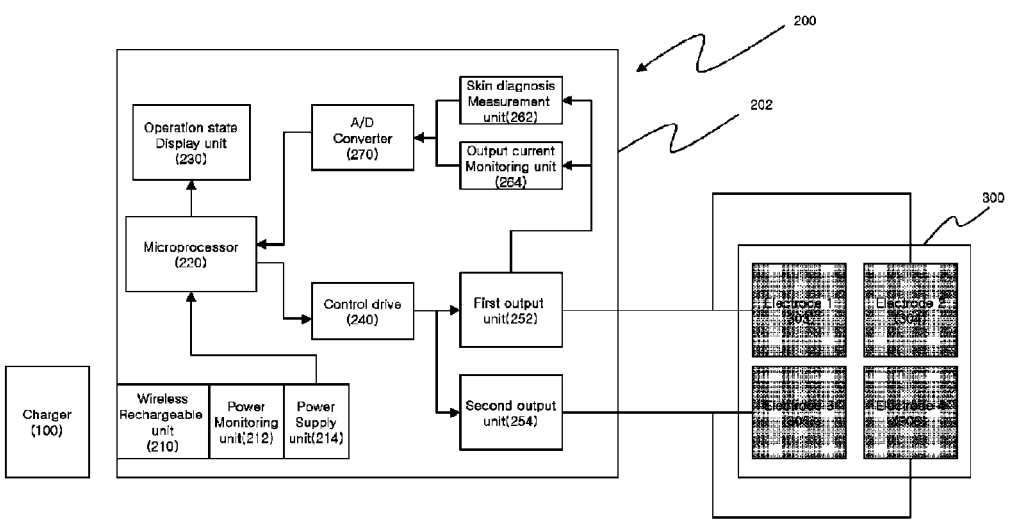

[Fig. 4]
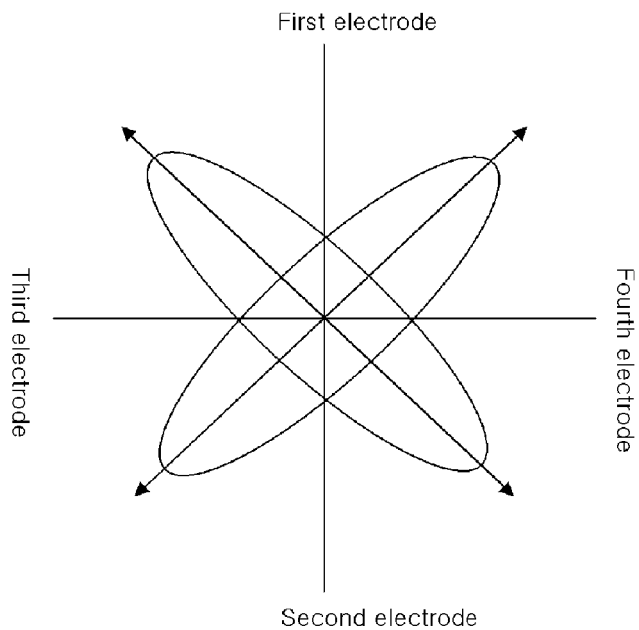
[Fig. 5]
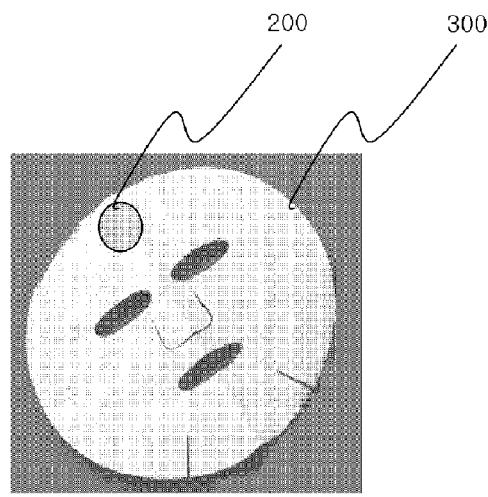
[Fig. 6]
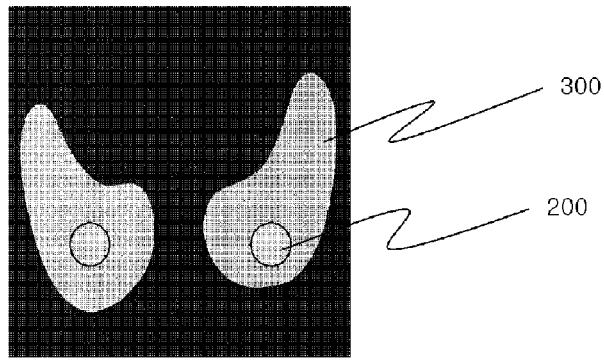

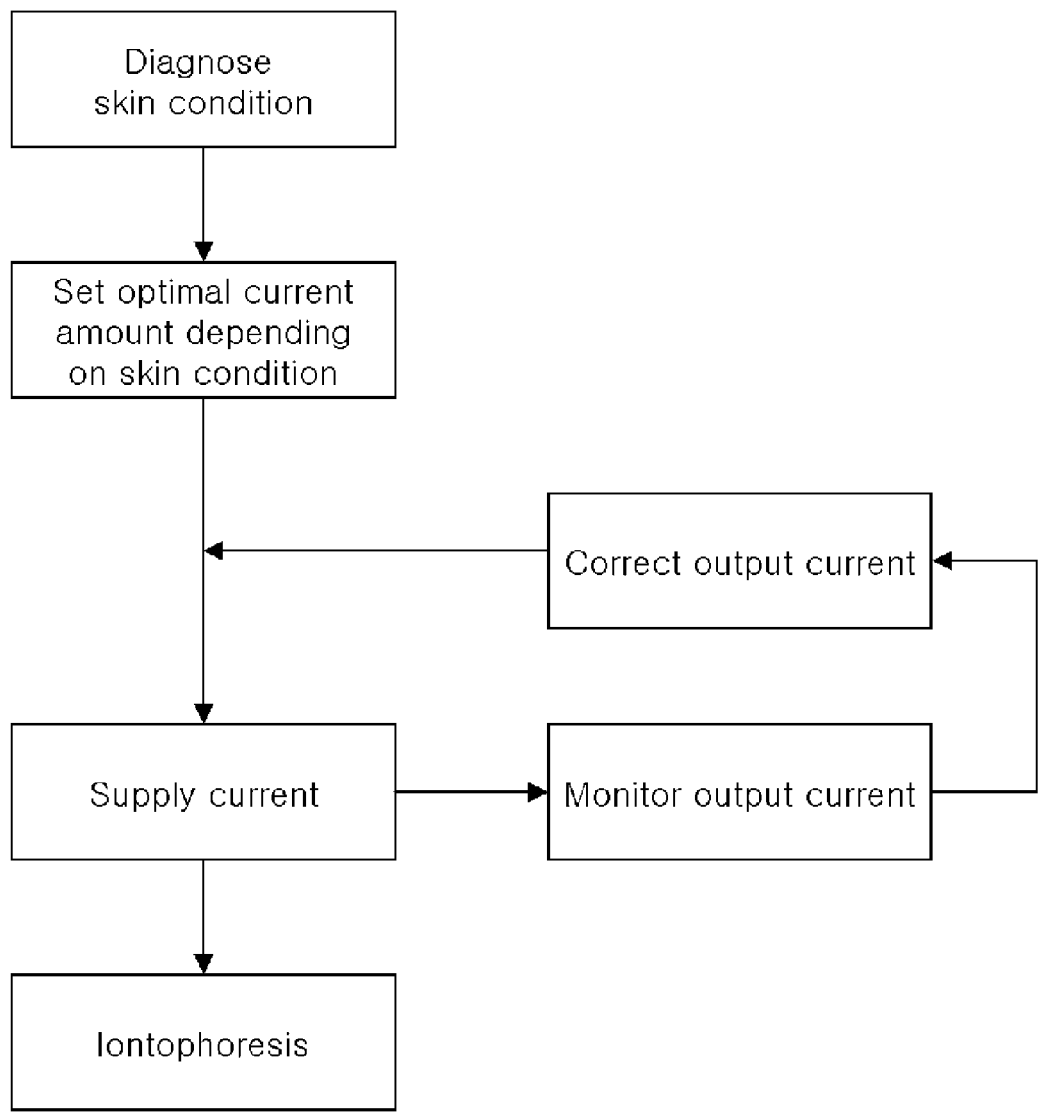
[Fig. 7]

APPARATUS FOR IONTOPHORESIS

TECHNICAL FIELD

The present invention relates to an iontophoresis apparatus, and more particularly, to an iontophoresis apparatus detachable from a mask or patch, wherein after skin condition is previously diagnosed before an iontophoresis is performed, the amount of current is adjusted according to the skin condition to absorb effective components contained in functional cosmetics or medicines into the skin, and a plurality of electrode pairs are applied to use interference current generated between the electrode pairs thereby accelerating absorption of the effective components and improving the skin condition.

BACKGROUND ART

Skin comprises epidermis, dermis, and subcutaneous adipose tissue. Since if cosmetics are applied to the skin, the epidermis, i.e., the upper layer of the skin, recognizes the cosmetics as a toxin and hinders absorption of the cosmetics due to the influence of molecular size, bio characteristics, biochemical phenomena, and the like, the amount of cosmetics practically absorbed into the skin is very small.

Accordingly, an iontophoresis method has been developed to increase absorption of cosmetics, medicines, or the like into the skin. The iontophoresis method is a method of allowing micro current to flow through the skin thereby absorbing effective components contained in the medicines or cosmetics having electric charges into the skin by electrical repulsive force. Such an iontophoresis method can be used so that vitamin C, which is a skin whitening effect material, is absorbed into the skin to eliminate liver spots or skin anti-aging materials is absorbed into the skin to suppress occurrence of wrinkles. Also, it has been known that the method is considerably effective.

Presently, iontophoresis apparatuses are marketed, which use a method of inducing electric fields to be formed around the skin by attaching patches allowing micro current to flow to the cheekbone area under the eyes after applying cosmetic components having superior antioxidant and skin protecting functions to the whole face.

However, such iontophoresis means are mainly manufactured as a disposable mask or patch having electrodes and batteries therein, so that the manufacturing costs are increased. Furthermore, since current intensity is fixed, there is a problem in that a side effect can occur if the current intensity is too high, and any effect cannot be obtained at all if the current is too low.

In order to solve the problems, disclosed in Korean Patent No. 610252 is a battery unit, which is detachably mounted to an electrode attached to skin of a user and comprises a battery housing for receiving batteries and an electric circuit capable of adjusting intensity of current so as to increase the amount of active materials absorbed into the skin of the user.

However, although such a battery unit can be detachably mounted to the electrode and save manufacturing costs, it is inconvenient in that skin condition of a user should be measured using a separate skin condition diagnosing apparatus in order to adjust current intensity in accordance with the skin condition of the user, and there is a problem in that whether the current flows constantly while the user uses the battery unit cannot be monitored.

DISCLOSURE OF INVENTION

Technical Problem

The present invention is conceived to solve the aforementioned problems. An object of the present invention is to provide an iontophoresis apparatus for improving skin condition of a user, wherein skin condition of a user is measured through electrodes attached to the skin of the user before an iontophoresis is performed, and an optimal amount of current appropriate for the measured skin condition of the user is generated to absorb effective components of medicines or cosmetics into the skin of the user.

Technical Solution

An iontophoresis apparatus according to the present invention for achieving the objects including a plurality of electrodes installed in a mask or patch attached to skin of a user, and an iontophoresis chip module configured to be detachably attached to a certain position of the mask or patch and electrically connected to the electrodes, wherein the iontophoresis chip module comprises a wireless rechargeable unit able to be charged in a non-contact charging manner; a microprocessor operating by the power received from the wireless rechargeable unit and storing a control program; a control drive for controlling voltage, frequency and current applied to the electrodes in response to a command of the microprocessor; an output unit connected to the control drive to transmitting constant current to the electrodes; a skin diagnosis measuring unit connected to the output unit and receiving bio-impedance of the user measured from the electrodes; and an A/D converter for converting analog data detected from the skin diagnosis measuring unit into digital data and inputting the converted digital data into the microprocessor.

Advantageous Effects

An iontophoresis apparatus according to the present invention has an effect in that after previously diagnosing skin condition of a user, an iontophoresis is performed using an optimal amount of current appropriate for the diagnosed skin condition of the user, whereby the skin condition of the user can be improved.

Furthermore, the iontophoresis apparatus of the present invention is effective in that two pairs of electrodes are used to further increase the effect of the iontophoresis through an interference phenomenon generated between the respective electrode pairs to thereby enhance the skin condition of the user.

BRIEF DESCRIPTION OF THE DRAWINGS

FIG. 1 is a block diagram showing an iontophoresis apparatus according to a first embodiment of the present invention.

FIG. 2 is a view showing a configuration between a rechargeable element and a wireless rechargeable unit when an iontophoresis apparatus according the present invention is charged.

FIG. 3 is a block diagram showing an iontophoresis apparatus according to a second embodiment of the present invention.

FIG. 4 is a graph showing a direction of interference current and an interference wave phenomenon generated between electrode pairs when an iontophoresis is performed using the iontophoresis apparatus shown in FIG. 3.

FIG. 5 is a picture showing a state where an iontophoresis chip module according to the present invention is attached to a mask.

FIG. 6 is a picture showing a state where the iontophoresis chip module according to the present invention is attached to a patch.

FIG. 7 is a flowchart schematically illustrating a process of performing an iontophoresis using the iontophoresis apparatus according to the present invention.

EXPLANATION OF REFERENCE NUMERALS FOR MAJOR PORTIONS SHOWN IN DRAWINGS

| | |
|---|---|
| 100: Charger | 200: Iontophoresis chip module |
| 202: Housing | 210: Wireless rechargeable unit |
| 212: Power monitoring unit | 214: Power supply unit |
| 216: Rechargeable element | 220: Microprocessor |
| 230: Operation state display unit | 240: Control drive |
| 250: Output unit | 252: First output unit |
| 254: Second output unit | |
| 262: Skin diagnosis measurement unit | |
| 264: Output current monitoring unit | |
| 270: A/D converter | |
| 300: Mask or patch | |
| 301, 302, 303, 304, 305, 306: Electrode | |

BEST MODE FOR CARRYING OUT THE INVENTION

Hereinafter, preferred embodiments of the present invention will be described in detail with reference to the accompanying drawings.

FIG. 1 is a block diagram showing an iontophoresis apparatus according to a first embodiment of the present invention, and FIG. 2 is a view showing a configuration between a rechargeable element and a wireless rechargeable unit when an iontophoresis apparatus according the present invention is charged.

Referring to FIG. 1, the iontophoresis apparatus according to the present invention comprises electrodes 301 and 302 provided in a mask or patch 300, which is manufactured to be attachable to skin of a user, to allowing current to flow to the user's skin, and an iontophoresis chip module 200 configured to be detachably attached to a certain part of the mask or patch 300 and electrically connected to the electrodes 301 and 302.

The iontophoresis chip module 200 comprises a wireless rechargeable unit 210 provided in a housing 202 to be charged without contacting to a charger 100, a power monitoring unit 212 connected to the wireless rechargeable unit 210 to monitor whether power is charged into the wireless rechargeable unit 210, a power supply unit 214 connected to the wireless rechargeable unit 210 to supply each unit with power charged in the wireless rechargeable unit 210, a microprocessor 220 supplied with power from the power supply unit 214 and storing a control program for controlling each unit, a control drive 240 for generating optimal voltage, current and frequency in response to a command of the microprocessor 220, an output unit 250 for outputting an optimal output value to the electrodes 301 and 302 connected through connectors in response to a control signal of the control drive 240, a skin diagnosis measuring unit 262 connected to the output unit 250 to receive bio-impedance of the user, i.e., skin resistance of the user, measured through the electrodes 301 and 302, and an analog-to-digital (A/D) converter 270 for converting a value input into the skin diagnosis measuring unit 262 from analog data into digital data and feeding back the converted digital data into the microprocessor 220.

The iontophoresis chip module 200 according to the present invention may further comprise an output current monitoring unit 264, which is connected to the output unit 250 and to which an output current value measured through the electrodes 301 and 302 is input. The output current monitoring unit 264 monitors whether constant current flows through the output unit 250, and then, corrects the output value so that constant current can flow through the microprocessor 220 if an error occurs.

The skin diagnosis measuring unit 262 measures the amount of moisture or sebum contained in the user's skin by measuring bio-impedance, i.e., skin resistance, through the electrodes attached to the user's skin before performing an iontophoresis, so that an appropriate amount of current can be output in accordance with the skin condition of the user.

The microprocessor 220, which stores a control program, adjusts current, voltage and frequency so that constant current can flow through the output unit 250, and controls an output method. Before an iontophoresis is performed, the current, voltage and frequency are set by feeding back the skin resistance of the user, which is input into the skin diagnosis measuring unit 262 from the output unit 250, to the microprocessor 220 through the A/D converter 270, so that an amount of current appropriate for the skin condition of the user can be output. In addition, while the iontophoresis is performed, the microprocessor 220 can measure, through the output current monitoring unit 264, whether constant current flows through the output unit 250, and then, correct the current, voltage and frequency so as to output constant current after receiving the measured current value.

The iontophoresis chip module 200 according to the present invention may further comprise a display unit 230 of various forms for showing an on/off state and a skin diagnosis state. The display unit 230 may be configured to have a plurality of light emitting diodes (LEDs), a liquid crystal display (LCD) or electro luminescence (EL) element, or the like. If LEDs or an EL element that emits light by itself is used, a usage state can be further more easily recognized and there is a further advantage in miniaturizing the apparatus. If an LED(s) is used, the skin diagnosis state displayed by the amount of current variously flowing through the output unit 250 in accordance with the skin diagnosis state can be displayed using a plurality of LEDs or one LED capable of emitting various colors. In addition to the on/off or skin diagnosis state, a charging state can be displayed while the apparatus is charged, and the degree of discharge can be displayed by blinking an LED while the apparatus is used.

A power switch (not shown) capable of turning on and off power of the iontophoresis chip module 200 may be additionally provided at a certain position of the display unit 230. Since the iontophoresis chip module 200 is manufactured in a relatively small size, it is preferred to control the on/off of the iontophoresis chip module 200 using the single power switch. In addition, the program can be set to proceed with a series of processes by the microprocessor 220 to perform an iontophoresis if power is turned on by manipulating the power switch and to automatically cut off the power if a predetermined time elapses.

FIG. 2 shows a view of charging the iontophoresis chip module 200 in a non-contact wireless charging method by allowing the iontophoresis chip module 200 to lie adjacent to the charger 100. This is a method of wirelessly transmitting energy, in which if the charger 100 is connected to an alternating current power source AC, alternating current is converted into direct current energy through a transformer and a rectifier, and then, the direct current energy is converted into the form of a sine wave with voltage boosted resonated through a high frequency resonant circuit device to flow through the primary coil L1. If the secondary coil L2 inside of the wireless rechargeable unit 210 lies adjacent to the primary coil L1, inductive current is generated between the primary coil L1 and the secondary coil L2. Therefore, the current flowing through the primary coil L1 is converted into a direct current component through the secondary coil L2 and a smoothing rectifier to thereby be charged into a rechargeable element 216.

Here, an ordinary rechargeable battery or condenser can be used as the rechargeable element 216, wherein the ordinary rechargeable battery or condenser may be individually used or both of them may be used together. A high capacity electric dual layer (EDL) condenser can be used as the condenser used in the rechargeable element 216. Since the EDL condenser is small in size compared with an ordinary battery, it is advantageous in manufacturing the iontophoresis chip module 200 in a small size.

Although recharging efficiency of the wireless recharging method is not so high, the power needed for operating the chip module can be sufficiently charged in a short time since consumption power used for the iontophoresis is not so much. Furthermore, since the rechargeable element is charged in a non-contact manner, a contact point does not need to be additionally formed in the chip module, and therefore, it is advantageous in that the apparatus can be further easily miniaturized and the rechargeable element can be conveniently charged.

FIG. 3 is a block diagram showing an iontophoresis apparatus according to a second embodiment of the present invention, and FIG. 4 is a graph showing a direction of interference current and an interference wave phenomenon generated between electrode pairs when an iontophoresis is performed using the iontophoresis apparatus shown in FIG. 3.

Referring to FIG. 3, it can be understood that the iontophoresis chip module of the second embodiment differs from the iontophoresis chip module 200 shown in FIG. 1 in the number of output units and in the number of electrodes formed on the mask or patch 300. Here, two pairs of electrodes 303, 304, 305 and 306 are used to improve iontophoresis effect by using the interference phenomenon generated between the two pairs of electrodes, which are respectively connected to a first output unit 252 and a second output unit 254 as shown in FIG. 4.

If two pairs of electrodes are used as described above, the microprocessor 220 can control the output method to be set to a variety of drive modes, which can be accomplished by setting frequencies, voltages and currents respectively output to the first output unit 252 and the second output unit 254 to the same value or different values. In addition, the electrodes 303, 304, 305 and 306 attached to the mask or patch 300 may be connected to either of the first output unit 252 or the second output unit 254.

Although it is respectively described in FIGS. 1 and 3 that a pair or two pairs of electrodes are used, the number of electrodes can be changed depending on the part of skin to be treated or the purpose of treatment.

FIG. 5 is a picture showing a state where an iontophoresis chip module according to the present invention is attached to a mask, and FIG. 6 is a picture showing a state where the iontophoresis chip module according to the present invention is attached to a patch.

Referring to FIGS. 5 and 6, the mask or patch 300 attached to the iontophoresis chip module 200 having the configuration shown in FIG. 1 or 3 is shown. A connector is additionally installed between the iontophoresis chip module 200 and the mask or patch 300 so that current output from the output unit of the iontophoresis chip module 200 can flow to the electrodes installed in the mask or patch 300.

The iontophoresis chip module 200 can be separately configured according to the ion component of cosmetics or medicines or to the purpose of the iontophoresis apparatus, and then selectively used appropriately to the ion component or the purpose.

In addition, the iontophoresis chip module 200 according to the present invention can be configured to integrate all constitutional components on a single chip, so that manufacturing of the iontophoresis chip module 200 can be simplified.

Hereinafter, a method of performing an iontophoresis according to the present invention will be described.

FIG. 7 is a flowchart schematically illustrating a process of performing an iontophoresis using the iontophoresis apparatus according to the present invention.

First, a user installs the iontophoresis chip module 200 to the mask or patch 300 and attaches the mask or patch 300 on the face or skin.

Thereafter, the user handles the power switch (not shown) installed on the iontophoresis chip module 200 to turn on the power.

If power is supplied to the iontophoresis chip module 200, bio-impedance, i.e., skin resistance, of a user is measured to diagnose skin condition using the program previously stored in the microprocessor 220. This is to measure the resistance of the body by allowing weak current to flow through the skin of the user, and the resistance can be varied depending on the amount of moisture in the body. For example, if the skin contains sufficient moisture, the passageway through which the current flows is widened and the resistance is thus measured small, whereas if the skin contains insufficient moisture, the passageway through which the current flows is narrowed and the resistance is thus measured large. In this manner, the amount of moisture contained in the skin can be measured.

The skin resistance of the user measured in this manner is measured through the electrodes provided within the mask or patch 300. The skin resistance is converted into digital data by the A/D converter 270 by way of the output unit 250 and the skin diagnosis measuring unit 262, and the converted digital data is transmitted to the microprocessor 220.

If the microprocessor 220 creates optimal voltage, current and frequency appropriate for the skin condition of the user using the skin resistance transmitted from the skin diagnosis measuring unit 262 and transmits the voltage, current and frequency to the control drive 240, the control drive 240 outputs an output having the optimal voltage, current and frequency through the output unit 250 and causes constant current to flow through the electrodes 301 and 302 connected to the output unit 250 to thereby perform an iontophoresis. At this time, if two pairs of electrodes are used, interference current is generated between the electrode pairs that are connected to the respective output units whereby the effect of the iontophoresis can be further improved.

While the iontophoresis is performed, whether constant current flows through the electrodes 301 and 302 is measured, and the measured result is transmitted to the output current monitoring unit 264 through the output unit 250. The measured result transmitted to the output current monitoring unit 264 is transmitted to the A/D converter 270 and converted from analog data to digital data. If the converted digital data is transmitted to the microprocessor 220, the microprocessor 220 checks whether or not the constant current normally flows. If an abnormal current flow is being detected, the microprocessor 220 compensates the voltage, current and frequency so that constant current can flow through the output unit 250.

If the programmed iontophoresis is completed, the microprocessor 220 issues a command for shutting down the power to the power supply unit 214.

If the power of the iontophoresis chip module 200 is turned off, the user detaches the iontophoresis chip module 200 from the mask or patch 300 and recharges the iontophoresis chip module 200 by allowing the iontophoresis chip module to lie adjacent to the charger 100.

Although the present invention has been described and illustrated in connection with the specific embodiments as described above, it will be readily understood that various modifications can be made thereto without departing from the scope of the present invention. Therefore, the scope of the present invention is not limited to the embodiments described above but is defined by the appended claims and the equivalents thereto.

INDUSTRIAL APPLICABILITY

An iontophoresis apparatus according to the present invention generates an optimal amount of current appropriate for skin condition of a user to absorb effective components of medicines or cosmetics into the skin of the user thereby being used for a variety of skin cosmetics.

The invention claimed is:

1. An iontophoresis apparatus comprising:
   a plurality of electrodes installed in a mask or patch configured to be attached to skin of a user; and
   an iontophoresis chip module configured to be detachably attached to a certain position of the mask or patch and electrically connected to the electrodes,
   wherein the iontophoresis chip module comprises:
      a wireless rechargeable unit able to be charged in a non-contact charging manner;
      a microprocessor operating by the power received from the wireless rechargeable unit and storing a control program;
      a control drive for controlling voltage, frequency and current applied to the electrodes in response to a command of the microprocessor;
      an output unit connected to the control drive to transmit constant current to the electrodes;
      a skin diagnosis measuring unit connected to the output unit and receiving bio-impedance of the user measured from the electrodes; and
      an A/D converter for converting analog data detected from the skin diagnosis measuring unit into digital data and inputting the converted digital data into the microprocessor,
   characterized in that the microprocessor sets optimal voltage, frequency and current to be applied to the electrodes based on bio-impedance of the user measured by the skin diagnosis measuring unit and controls the output unit through the control drive,
   wherein the output unit comprises first and second output units separately controlled by the microprocessor, the electrodes are configured in two pairs, and the two pairs of electrodes are connected to the first and second output units respectively, and
   wherein the microprocessor is configured to control the first and second output units to output current in wave form to the two pairs of electrodes, said current waves transmitted to the two pairs of electrodes in phased interference to each other thereby creating a wave interference phenomena for accelerating the iontophoresis effect.

2. The apparatus as claimed in claim 1, wherein the iontophoresis chip module further comprises an output current monitoring unit connected to the output unit to receive an output current value measured from the electrodes, and transmits the measured output current value to the microprocessor through the A/D converter.

3. The apparatus as claimed in claim 1, wherein the iontophoresis chip module further comprises a display unit for displaying an operational state of the apparatus and a state of skin diagnosis.

4. The apparatus as claimed in claim 3, wherein the display unit comprises a light emitting diode (LED).

5. The apparatus as claimed in claim 1, wherein the wireless rechargeable unit uses a rechargeable battery or condenser as a recharging means.

6. The apparatus as claimed in claim 1, wherein the wireless rechargeable unit uses a rechargeable battery and a condenser together as a recharging means.

7. The apparatus as claimed in claim 6, wherein the condenser is an electric dual layer (EDL) condenser.

8. The apparatus as claimed in claim 1, wherein the wireless rechargeable unit uses an electric dual layer (EDL) condenser as a recharging means.

9. The apparatus as claimed in claim 1, wherein all components of the iontophoresis chip module are integrated in a single chip.

* * * * *